US009339548B2

(12) United States Patent
Hsu

(10) Patent No.: US 9,339,548 B2
(45) **Date of Patent: *May 17, 2016**

(54) THERMO-SENSITIVE, MUCOADHESIVE OR DERMOADHESIVE, AND PENETRATION-ENHANCING FORMULATIONS FOR TOPICAL DELIVERY OF THERAPEUTICS

(71) Applicant: UNIVERSITY OF FLORIDA RESEARCH FOUNDATION, INC., Gainesville, FL (US)

(72) Inventor: Stephen I-Hong Hsu, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/739,334

(22) Filed: Jun. 15, 2015

(65) Prior Publication Data

US 2015/0273072 A1 Oct. 1, 2015

Related U.S. Application Data

(63) Continuation of application No. 14/008,004, filed as application No. PCT/US2012/031084 on Mar. 29, 2012, now Pat. No. 9,056,137.

(60) Provisional application No. 61/470,551, filed on Apr. 1, 2011, provisional application No. 61/602,769, filed on Feb. 24, 2012.

(51) Int. Cl.

| | |
|---|---|
| ***A61K 9/14*** | (2006.01) |
| ***A61K 47/34*** | (2006.01) |
| ***A61K 31/74*** | (2006.01) |
| ***A61K 38/10*** | (2006.01) |
| ***A61K 38/20*** | (2006.01) |
| ***A61K 38/28*** | (2006.01) |
| ***A61K 47/10*** | (2006.01) |
| ***A61K 47/22*** | (2006.01) |
| ***A61K 31/37*** | (2006.01) |
| ***A61K 31/4439*** | (2006.01) |
| ***A61K 31/5377*** | (2006.01) |
| ***A61K 31/7024*** | (2006.01) |
| ***A61K 31/727*** | (2006.01) |
| ***A61K 31/155*** | (2006.01) |
| ***A61K 31/64*** | (2006.01) |
| ***A61K 9/00*** | (2006.01) |
| ***A61K 31/18*** | (2006.01) |
| ***A61K 31/427*** | (2006.01) |
| ***A61K 31/451*** | (2006.01) |
| ***A61K 31/4965*** | (2006.01) |
| ***A61K 31/55*** | (2006.01) |
| ***A61K 31/702*** | (2006.01) |

(Continued)

(52) U.S. Cl.

CPC ............... *A61K 47/34* (2013.01); *A61K 9/0014* (2013.01); *A61K 9/0034* (2013.01); *A61K 31/155* (2013.01); *A61K 31/18* (2013.01); *A61K 31/37* (2013.01); *A61K 31/427* (2013.01); *A61K 31/4439* (2013.01); *A61K 31/451* (2013.01); *A61K 31/4965* (2013.01); *A61K 31/5377* (2013.01); *A61K 31/55* (2013.01); *A61K 31/64* (2013.01); *A61K 31/702* (2013.01); *A61K 31/7024* (2013.01); *A61K 31/727* (2013.01); *A61K 31/74* (2013.01); *A61K 38/10* (2013.01); *A61K 38/2013* (2013.01); *A61K 38/28* (2013.01); *A61K 39/00* (2013.01); *A61K 39/0002* (2013.01); *A61K 39/0011* (2013.01); *A61K 39/02* (2013.01); *A61K 39/12* (2013.01); *A61K 39/35* (2013.01); *A61K 45/06* (2013.01); *A61K 47/10* (2013.01); *A61K 47/22* (2013.01); *A61K 9/006* (2013.01); *A61K 2039/54* (2013.01); *A61K 2039/541* (2013.01)

(58) Field of Classification Search

CPC ..................................................... A61K 47/34

See application file for complete search history.

(56) References Cited

U.S. PATENT DOCUMENTS

| | | | |
|---|---|---|---|
| 6,309,663 | B1 | 10/2001 | Patel et al. |
| 6,503,955 | B1 | 1/2003 | Dobrozsi et al. |

(Continued)

FOREIGN PATENT DOCUMENTS

| | | |
|---|---|---|
| CN | 1435261 | 8/2003 |
| CN | 101518562 | 9/2009 |

(Continued)

OTHER PUBLICATIONS

Paek, S.H., et al., "Poloxamer 188 and Propylene Glycol-Based Rectal Suppository Enhances Anticancer Effect of 5-Fluorouracil in Mice," *Biological and Pharmaceutical Bulletin*, 2006, vol. 29, No. 5, pp. 1060-1063.

(Continued)

*Primary Examiner* — Paul Dickinson

(74) *Attorney, Agent, or Firm* — Saliwanchik, Lloyd & Eisenschenk

(57) ABSTRACT

The present invention provides thermo-sensitive, mucoadhesive biopolymer formulations that enhance the penetration of therapeutics across the skin or mucosal surfaces. In a preferred embodiment, the biopolymer formulation comprises co-polymer of poloxamer 188 and propylene glycol, laurocapram and, optionally, one or more therapeutic agents. Also provided are uses of the biopolymer formulations for topical therapy of cancer including cervical cancer.

7 Claims, 2 Drawing Sheets

(51) Int. Cl.

| | |
|---|---|
| ***A61K 39/00*** | (2006.01) |
| ***A61K 39/02*** | (2006.01) |
| ***A61K 39/12*** | (2006.01) |
| ***A61K 39/35*** | (2006.01) |
| ***A61K 45/06*** | (2006.01) |

(56) References Cited

U.S. PATENT DOCUMENTS

| | | | | |
|---|---|---|---|---|
| 9,056,137 | B2 | 6/2015 | Hsu | |
| 2004/0009212 | A1 | 1/2004 | Tsai | |
| 2004/0131625 | A1 * | 7/2004 | Berthet et al. | 424/184.1 |
| 2005/0222034 | A1 | 10/2005 | Hsu | |
| 2005/0244502 | A1 | 11/2005 | Mathias et al. | |
| 2008/0153900 | A1 | 6/2008 | Hunter | |
| 2010/0183519 | A1 | 7/2010 | Katz et al. | |
| 2010/0203144 | A1 | 8/2010 | Laurencin et al. | |

FOREIGN PATENT DOCUMENTS

| | | |
|---|---|---|
| EP | 1 332 764 | 12/2005 |
| EP | 2 278 956 | 9/2011 |
| JP | 2003-509350 | 3/2003 |
| JP | 2003-510279 | 3/2003 |
| JP | 2005-505590 | 2/2005 |
| JP | 2009-221186 | 10/2009 |
| WO | WO 01/22967 | 4/2001 |
| WO | WO 03/030877 | 4/2003 |
| WO | WO 2010/040632 | 4/2010 |

OTHER PUBLICATIONS

Written Opinion in International Application No. PCT/US2012/031084, Oct. 25, 2012, pp. 1-3.

Stoughton, R.B. "Enhanced Percutaneous Penetration With 1-Dodecylazacycloheptan-2-one" *Arch Dermatol*, Jul. 1982, pp. 474-477, vol. 118.

Stoughton, R.B. et at. "Azone®: A New Non-Toxic Enhancer of Cutaneous Penetration" *Drug Development and Industrial Pharmacy*, 1983, pp. 725-744, vol. 9 No. 4.

Kaushik, D. et at. "Percutaneous permeation modifiers: enhancement versus retardation" *Expert Opinion Drug Delivery*, 2008, pp. 1-13, vol. 5, No. 5.

Spruance, S.L. et at. "Effect of Azone and Propylene Glycol on Penetration of Trifluorothymidine Through Skin and Efficacy of Different Topical Formulations Against Cutaneous Herpes Simplex Virus Infections in Guinea Pigs" *Antimicrobial Agents and*R5 *Chemotherapy*, Dec. 1984, pp. 819-823, vol. 26, No. 6.

Kaushik, D. et at. "Percutaneous penetration modifiers and formulation effects" *International Journal of Pharmaceutics*, 2010, pp. 42-51, vol. 386.

Kaushik, D. et at. "Percutaneous Penetration Modifiers and Formulation Effects: Thermal and Spectral Analyses" *AAPS PharmSci Tech*, Sep. 2010, pp. 1068-1063, vol. 11, No. 3.

* cited by examiner

```
                       SEQUENCE LISTING

<160> NUMBER OF SEQ ID NOS: 2

<210> SEQ ID NO 1
<211> LENGTH: 18
<212> TYPE: PRT
<213> ORGANISM: Homo sapiens

<400> SEQUENCE: 1

Ala Thr Gly Cys Leu Leu Asp Asp Gly Leu Glu Gly Leu Phe Glu Asp
1               5                   10                  15

Ile Asp

<210> SEQ ID NO 2
<211> LENGTH: 18
<212> TYPE: PRT
<213> ORGANISM: Homo sapiens
<220> FEATURE:
<221> NAME/KEY: MISC_FEATURE
<223> OTHER INFORMATION: PHD/bromodomain interacting region from human
      TRIP-Br2

<400> SEQUENCE: 2

Thr Gly Phe Leu Thr Asp Leu Thr Leu Asp Asp Ile Leu Phe Ala Asp
1               5                   10                  15

Ile Asp
```

THERMO-SENSITIVE, MUCOADHESIVE OR DERMOADHESIVE, AND PENETRATION-ENHANCING FORMULATIONS FOR TOPICAL DELIVERY OF THERAPEUTICS

CROSS REFERENCE TO RELATED APPLICATIONS

This application is a continuation of U.S. Ser. No. 14/008,004, filed Sep. 27, 2013, now U.S. Pat. No. 9,056,137, which is the U.S. national stage application of International Patent Application No. PCT/US2012/031084, filed Mar. 29, 2012, which claims the benefit of U.S. Provisional Patent Application Ser. No. 61/470,551, filed Apr. 1, 2011, and Ser. No. 61/602,769, filed Feb. 24, 2012 the disclosures of which are hereby incorporated by reference in their entireties, including all figures, tables and nucleic acid sequences.

The Sequence Listing for this application is labeled "Seq-List.txt" which was created on Mar. 28, 2012 and is 1 KB. The entire contents of the sequence listing is incorporated herein by reference in its entirety.

BACKGROUND

Cervical cancer is a fatal disease if not detected and treated early. 99.7% of cervical cancer cases are etiologically associated with at least one of 15-18 oncogenic types of human papillomavirus (4-6). Over 85% of cervical cancer occurs in developing countries and other historically underserved low-resource populations where it is the leading cause of death from cancer among women (1). Most high-grade cervical cancer can be prevented if pre-cancerous lesions or early-stage cervical cancer becomes diagnosed and treated.

At present, pre-cancerous lesions or early-stage cervical cancer can be detected using inexpensive screening methods, such as visual inspection of the cervix using acetic acid (vinegar) or Lugol's solution (iodine), or by using a new and affordable HPV-DNA test (careHPV, Qiagen) that can detect 14 high-risk types of HPV. However, there is a lack of affordable therapies for pre-cancerous cervical dysplasia. The costly and invasive therapies currently in use (cryotherapy, cone biopsies and loop electrosurgical excision procedure) all require both an established clinical infrastructure as well as highly trained medical personnel typically in the form of a dedicated gynecologic oncology service. Such resources are unavailable to large high-risk populations who have neither the economic means nor transportation options to access such clinical services. Thus, while limitations to screening in low resource settings appear to have been adequately addressed, there remains an unmet and urgent global need for an alternative therapy for those who have positive test results. The remaining challenge is to create a novel therapy for pre-cancerous cervical dysplastic lesions caused by high-risk types of HPV and prevent their progression to carcinoma in situ and/or invasive cervical cancer. Such a therapy should be inexpensive, easily self-administered or readily applied with assistance by a trained healthcare worker in a local clinic, and be effective as a single dose therapy that can be used in a single visit "screen, treat and prevent" public healthcare model that can be implemented even in the most impoverished populations where extremes of temperature may exist, space is limited and running water and electricity are unavailable.

BRIEF SUMMARY

The present invention provides novel co-polymer and drug penetration-enhancer formulations as a non-invasive delivery system for direct topical delivery of one or more chemotherapeutic agents for the treatment of cervical dysplasia aimed at preventing progression to carcinoma in situ and/or invasive cervical cancer. Advantageously, the co-polymer/enhancer formulations of the present invention are thermo-sensitive, mucoadhesive or dermoadhesive, and enhance the penetration of small and large therapeutically active compounds such as proteins greater than 52 amino acids across normal or diseased skin (transdermal delivery) or mucosa (transmucosal delivery). These properties facilitate the delivery of stable and active compounds contained in such co-polymer/enhancer formulations with properties that allow them to be solid phase at room temperature for ease of insertion and directed application to the cervical transformation zone, instantly melt at physiological temperature, adhere to mucosa and enhance the penetration of a chemotherapeutic drug across the entire dysplastic squamous epithelium. In a preferred embodiment, the co-polymer/enhancer formulations comprise a mixture of poloxamer 188 (P188), propylene glycol (PG) and laurocapram (LP) that can be customized and optimized for the delivery of one or more therapeutic agents or compounds.

In addition, the present invention provides uses of co-polymer/enhancer formulations for thermo-sensitive, dermoadhesive or mucoadhesive and penetration-enhanced topical delivery of a broad range of compounds to treat both neoplastic and non-neoplastic proliferative lesions of the skin or mucosal surfaces. In certain embodiments, the co-polymer/enhancer formulation of the present invention enhances delivery of therapeutic agents across normal or diseased skin or mucosal surfaces including, but not limited to, cervix, vagina, vulva, anus, rectum, eye, ear, oral cavity, nasopharynx, larynx, and head and neck for topical therapy.

In one embodiment, the present invention can be used for treatment of neoplastic and non-neoplastic proliferative diseases including, but not limited to, HPV-associated cervical lesions such as pre-cancerous low-grade cervical dysplasia including cervical intraepithelial neoplasia stage I or II (CIN I, CIN II) and high-grade dysplasia (CIN III); vulvar cancer; vaginal cancer or tumor; endometrial cancer; laryngeal carcinoma; head and neck cancer; skin cancer; skin tags; common HPV-associated warts of the hands, feet and extremities; and psoriasis.

In one embodiment, the present invention may be used as a transdermal or transmucosal deliver system (or device) for small and large therapeutic compounds and biomolecules into subcutaneous or submucosal tissue, or into the systemic circulation as an alternative to subcutaneous injections with needles or intravenous delivery with indwelling catheters.

BRIEF DESCRIPTION OF THE SEQUENCES

Figure 1:
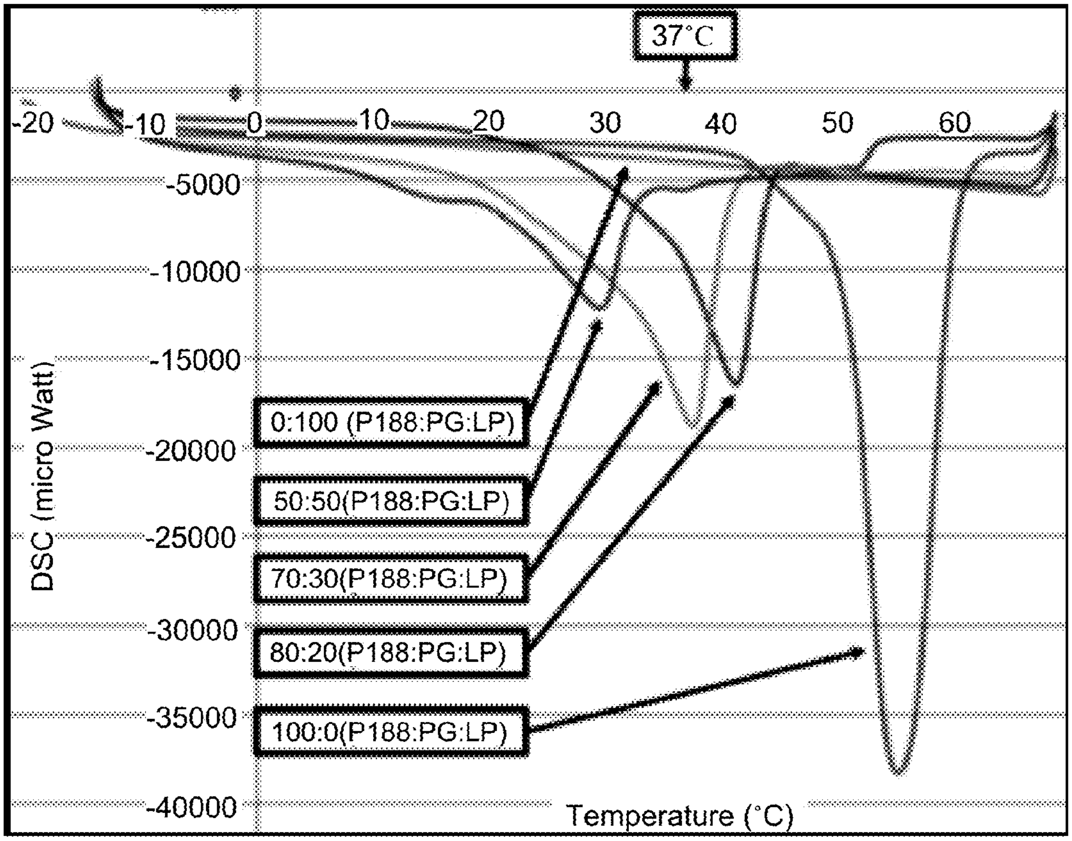
FIG. 1 shows a thermal profile of the *Br1-containing P188/PG/LP co-polymer/enhancer formulation. Differential Scanning calorimetry curves show the thermal property of the drug delivery formulation, which contains 1 mM *Br1, a 38 amino acid cytotoxic peptide, in various proportions of poloxamer 188 (P188) and propylene glycol (PG) with the addition of 0.4 M laurocapram (LP).

SEQ ID NO: 1 is an amino acid sequence of a TRIP-Br1 decoy peptide (*Br1).

SEQ ID NO: 2 is an amino acid sequence of a TRIP-Br2 decoy peptide (*Br2).

DETAILED DESCRIPTION OF THE INVENTION

The present invention provides co-polymer/enhancer formulations for topical and transdermal or transmucosal delivery of compounds. Advantageously, the co-polymer/enhancer formulations of the present invention are thermo-sensitive, mucoadhesive or dermoadhesive, and enhance the penetration of therapeutics across skin or mucosal surfaces. Also provided are therapeutic uses of the co-polymer/enhancer co-polymer/enhancer formulations for topical treatment of cancer, including cervical cancer.

In a preferred embodiment, the delivery system comprises co-polymers of poloxamer 188 (P188) and propylene glycol, the penetration-enhancer laurocapram and, optionally, one or more therapeutic agents. In a preferred embodiment, the delivery formulation of the present invention can be used for topical delivery of large cytotoxic peptides, such as TRIP-Br decoy peptides including the TRIP-Br1 decoy peptide (*Br1) and/or the TRIP-Br2 decoy peptide (*Br2). TRIP-Br decoy peptides target disruption of the TRIP-Br integrator function at E2F-responsive promoters, which induces a novel mechanism of cell death in proliferating cells (8-10); therefore, topical delivery of the TRIP-BR decoy peptides according to the present invention not only provides local therapy of pre-cancerous cervical dysplasia, but also prevents progression of pre-cancerous conditions to cervical cancer.

As demonstrated in the Example, the co-polymer/enhancer formulations of the present invention are thermo-sensitive; that is, solid at room temperature for ease of insertion into the cervical transformation zone and instantly melt at physiological temperature. Furthermore, the co-polymer/enhancer formulations adhere to and enhance peptide penetration across cervical mucosa.

In one embodiment, the present invention can be used for topical therapy of human HPV-associated low-grade cervical dysplasia defined cytologically as cervical intraepithelial neoplasia stage I or II (CIN I, CIN II) or for high-grade dysplasia (CIN III) to prevent progression to carcinoma in situ (CIS) and invasive cervical cancer (11).

Advantageously, the co-polymer/enhancer formulations of the present invention allow for non-invasive, targeted delivery of therapeutics across the skin and mucosal surfaces. Additionally, the present co-polymer/enhancer formulations use safe, inexpensive ingredients, are easy to administer and are suitable for use in a wide range of clinical settings. The co-polymer/enhancer formulations can easily be administered by healthcare workers or by self-administration by the patient, and under conditions of extreme temperature, high humidity, poor lighting, lack of space or lack of adequate supply of electricity or water.

Co-Polymer/Enhancer Formulation for Topical Delivery of Therapeutic Compounds One aspect of the invention provides co-polymer/enhancer formulations for topical delivery of therapeutics. Advantageously, the co-polymer/enhancer formulations of the present invention are thermo-sensitive, mucoadhesive or dermoadhesive, and enhance the penetration of therapeutics across the full thickness of the skin or mucosal surfaces.

In one embodiment, the novel topical delivery formulation comprises a thermo-sensitive polymer, a mucoadhesive or dermoadhesive polymer, a penetration enhancer and, optionally, one or more therapeutic agents.

In one embodiment, the co-polymer/enhancer formulation comprises co-polymer of one or more thermosensitive polymers, one or more mucoadhesive or dermoadhesive polymers and one or more penetration-enhancing agents. In a preferred embodiment, the co-polymer/enhancer formulation comprises co-polymer of poloxamer 188 and propylene glycol, the penetration-enhancer laurocapram and, optionally, one or more therapeutic agents.

In one embodiment, the co-polymer/enhancer formulation comprises one or more polymeric materials including, but not limited to, poloxamer and poloxamine. Poloxamers useful according to the present invention include, but are not limited to, poloxamer 188, 407, 101, 105, 108, 122, 123, 124, 181, 182, 183, 184, 185, 212, 215, 217, 231, 234, 235, 237, 238, 282, 284, 288, 331, 333, 334, 335, 338, 401, 402, and 403. Poloxamines useful according to the present invention include, but are not limited to, poloxamine 304, 504, 701, 702, 704, 707, 901, 904, 908, 1101, 1102, 1104, 1301, 1302, 1304, 1307, 1501, 1502, 1504, and 1508.

In certain embodiments, the co-polymer/enhancer formulation can comprise one or more polymeric materials including, but not limited to, polylactic acid and copolymers, polyvinyl acetate, celluloses and derivatives (such as carboxymethyl cellulose, cellulose acetate, cellulose acetate propionate, ethyl cellulose, hydroxypropyl methyl cellulose, hydroxyalkyl methyl celluloses and alkyl celluloses), crosslinked dextrans, polyethylene glycol, diethylaminoethyl dextran, poly(cyanoacrylates), copolymers of PEG and PLA, poly(lactic-co-glycolic acid), poly(ortho esters) and hydrogels. Preferably, the polymeric material is pharmaceutically-acceptable, biodegradable, mucoadhesive or dermoadhesive and/or enhances the penetration of therapeutics across the skin and/or mucosal surface.

In one embodiment, the co-polymer/enhancer formulation further comprises one or more mucoadhesive or dermoadhesive agents. In one embodiment the mucoadhesive or dermoadhesive agent promotes adhesion of the co-polymer/enhancer formulation to the skin or mucosa membranes, e.g., cervical epithelium. Preferably, the mucoadhesive or dermoadhesive agent also enhances the penetration of therapeutics across the skin and/or mucosal surface.

Mucoadhesive or dermoadhesive agents useful according to the present invention include, but are not limited to, polyols such as, propylene glycol, dipropylene glycol, polyethylene glycol, glycerine and butylene glycol; glycol derivatives with glycerol esters, such as, oleic acid esters of propylene glycol; and non-ionizable glycol ether derivatives, such as, ethoxydiglycol.

Mucoadhesive or dermoadhesive agents useful according to the present invention, can also include polymers such as, polyethylene glycol caprylic/capric glycerides; vinyl polymers (e.g., polyhydroxyethyl acrylate, polyhydroxyethyl methacrylate, polyvinyl alcohol and polyvinyl pyrrolidone); cellulosic derivatives, such as, methyl cellulose, ethyl cellulose, hydroxyethyl cellulose, hydroxypropyl cellulose, hydroxypropylmethyl cellulose and carboxymethyl cellulose; polysaccharides, such as, alginic acid and sodium alginate.

In one embodiment, the topical delivery formulation further comprises one or more penetration enhancers. Penetration enhancers useful according to the present invention include, but are not limited to, laurocapram, diethylene glycol, monoethyl ether, n-decyl methyl sulfoxide, dimethyl sulfoxide, dimethylacetamidedimethylformamide, sucrose monooleate, amides and other nitrogenous compounds (e.g., urea, 2-pyrrolidone, 1-methyl-2-pyrrolidone, ethanolamine, diethanolamine and triethanolamine), organic acids (e.g., citric acid and succinic acid), N-methyl-2-pyrrolidine, borage oil, tetrahydropiperine (THP), alcohols (e.g., methanol, ethanol, propanol, octanol, benzyl alcohol, myristyl alcohol, cetyl alcohol, stearyl alcohol), fatty acids (e.g., oleic acid), fatty acid esters (e.g., isopropyl myristate, isopropyl palmitate), polyols (e.g., propylene glycol, polyethylene glycol, glycerol), polyethylene glycol monolaurate and lecithin.

In one embodiment, the penetration modifier can either enhance or retard penetration when combined with specific mucoadhesive or dermoadhesive agents such that, for example, it acts as a penetration enhancer in combination with propylene glycol but it acts as a penetration retardant in combination with polyethylene glycol. A co-polymer/retardant formulation may be used to prevent penetration across the skin or mucosal surfaces of harmful compounds including but not limited to toxins released during an environmental accident or catastrophe. In this embodiment, such co-polymer/retardant formulations may serve as a form of personal protection or as a medical countermeasure (MCM) for chemical, biological, radiological, and nuclear agents, as well as the for infectious agents, pandemic influenza and other emerging infectious diseases.

Preferably, the co-polymer/enhancer formulation is solid or semi-solid at room temperature and melts at a temperature slightly below physiological temperatures. Generally, room temperature is below 30° C., below 28° C., below 25° C., below 23° C., below 20° C., or below 18° C.

In certain embodiments, the co-polymer/enhancer formulation melts, or begins to melt, at a temperature ranging from about 30° C. to 42° C., 32° C. to 40° C., 33° C. to 40° C., 35° C. to 38° C., or 34° C. to 37° C. In certain embodiments, the co-polymer/enhancer formulation melts, or begins to melt, at a temperature above 30° C., 31° C., 32° C., 33° C., 34° C., 35° C., 36° C., or 37° C. In certain embodiments, the biopolymer formulation melts, or begins to melt, at a temperature below 45° C., 44° C., 43° C., 42° C., 41° C., 40° C., 39° C., 38° C., 37° C., 36° C., 35° C., or 34° C.

The desired thermal property of the co-polymer/enhancer formulation can be achieved by adjusting the relative ratio (e.g., in terms of weight percentages or molar amounts) of various ingredients including, the thermo-sensitive polymeric material, the mucoadhesive agent, the penetration enhancer and/or the therapeutic agent.

In certain embodiments, the co-polymer/enhancer formulation comprises a polymeric material at a weight percentage of about 20% to about 95%, about 25% to about 90%, about 30% to about 85%, about 35% to about 80%, about 40% to about 70%, about 50% to about 90%, about 50% to about 85%, about 60% to about 80%, about 30% to about 40%, about 30% to about 50%, about 70% to about 90%, about 70% to about 85% or about 70% to about 80%.

In certain embodiments, the co-polymer/enhancer formulation comprises a mucoadhesive or dermoadhesive agent at a weight percentage of about 5% to about 90%, about 10% to about 80%, about 10% to about 70%, about 10% to about 60%, about 10% to about 50%, about 10% to about 40%, about 10% to about 35%, about 10% to about 30%, about 10% to about 20%, about 5% to about 30%, about 5% to about 20%, about 5% to about 15% or about 15% to about 30%.

In certain embodiments, the co-polymer/enhancer or co-polymer/retardant formulation comprises a penetration enhancer or penetration retardant, respectively, at a concentration ranging from about 0.1 M to about 1 M, about 0.2 M to about 0.9 M, about 0.3 M to about 0.8 M, about 0.4 M to about 0.7 M, or about 0.2 M to about 0.5 M.

In certain embodiments, the co-polymer/enhancer or co-polymer/retardant formulation comprises a penetration enhancer or penetration retardant, respectively, at a concentration above 0.05 M, 0.1 M, 0.15 M, 0.2 M, 0.3 M, 0.4 M, 0.5 M, 0.6 M, 0.7 M, 0.8 M, 0.9 M, 1.0 M, 1.5 M, 2 M, 2.5 M or 3 M.

In certain embodiments, the co-polymer/enhancer or co-polymer/retardant formulation comprises a penetration enhancer or penetration retardant, respectively, at a concentration below 7 M, 6 M, 5 M, 4.5 M, 4 M, 3.5 M, 3 M, 2.5 M, 2 M, 1.5 M, 1 M, 0.9 M, 0.8 M, 0.7 M, 0.6 M or 0.5 M.

In certain specific embodiments, the co-polymer/enhancer formulation comprises poloxamer 188 and propylene glycol at a ratio (w/w) of about 100:0, 90:10, 80:20, 70:30, 60:40, 50:50, 40:60, 30:70, 20:80, 10:90, or 0:100. In preferred embodiments, the co-polymer/enhancer formulation comprises poloxamer 188 and propylene glycol at a ratio (w/w) of about 70:30 (37° C., core body temperature) or 65/35 (34° C., skin temperature).

In certain embodiments, the co-polymer/enhancer formulation comprises laurocapram at a concentration of about 0.1 M to about 1 M, about 0.2 M to about 0.9 M, about 0.3 M to about 0.8 M, about 0.4 M to about 0.7 M or about 0.2 M to about 0.5 M. In a preferred embodiment, the co-polymer/enhancer formulation comprises about 0.4 M laurocapram.

The co-polymer/enhancer formulation can be used for topical delivery of a variety of small or large therapeutic agents not previously achieved using penetration enhancers including, but not limited to, large peptides and proteins greater than 52 amino acids, nucleic acids, compounds with unique physicochemical structures and/or properties not considered amenable to transdermal or transmucosal delivery, chemotherapeutic agents, anti-cancer or anti-tumor agents, antibiotics, anti-bacterial agents, anti-viral agents, anti-fungal agents, anti-microbial agents, anti-neoplastic agents, immunomodulatory agents, anti-inflammatory agents, cytokines and chemokines (e.g. interleukins), agents suitable for the treatment of diabetes such as insulin preparations with or without secretagogues and/or thiazolidinediones, agents suitable for acute and/or chronic anti-coagulation (e.g. low-molecular weight heparin), and vaccine antigens currently administered by subcutaneous or intramuscular needle injection or intravenous delivery through an indwelling catheter. In a preferred embodiment the co-polymer/enhancer formulations are useful for topical delivery of therapeutic agents for treatment of cervical dysplasia and for transdermal or transmucosal delivery of large therapeutic biomolecules such as insulin, anti-thrombotic agents and vaccine antigens.

Conversely, co-polymer/retardant formulations can be used to prevent penetration across the skin or mucosal surfaces of harmful compounds including but not limited to toxins released during an environmental accident or catastrophe. In this embodiment, such co-polymer/retardant formulations may serve as a form of personal protection or as a medical countermeasure (MCM) for chemical, biological, radiological, and nuclear agents, as well as the for infectious agents, pandemic influenza and other emerging infectious diseases.

Examples of decoy peptides useful in the disclosed formulations include, but are not limited to, TRIP-Br decoy peptides including TRIP-Br1 decoy peptide (*Br1) (ATGCLLDDGLEGLFEDID) (SEQ ID NO: 1) and TRIP-Br2 decoy peptide (*Br2) (TGFLTDLTLDDILFADID) (SEQ ID NO: 2), which are described in U.S. Pat. No. 7,223,733 (see claims 1-5).

Examples of chemotherapeutics and anti-cancer/anti-tumor agents useful in the disclosed formulations include, but are not limited to, 5-fluorouracil, chlorambucil, aminolevulinic acid, altretamine, ambomycin, vincristine, buthionine sulfoximine, asparaginase, bleomycin, busulin, trimetrexate, adriamycin, taxotere, carboplatin, cisplatin, carmustine, cladribine, 5-ethynyluracil, 9-dihydrotaxol, mitomycin, abiraterone, acivicin, teniposide, aclarubicin, acodazole hydrochloride, canarypox IL-2, acronine, thioguanine, acylfulvene, adecypenol, adozelesin, aldesleukin, thiotepa, ambamustine, busulfan, ametantrone acetate, amidox, amrubicin, mercaptopurine, cyclophosphamide, cytarabine, paclitaxel, pentostatin, dacarbazine, dactinomycin, daunorubicin, camptothecin derivatives, doxorubicin, etoposide, fludarabine phosphate, hydroxyurea, BRC/ABL antagonists, breflate, brequinar sodium, bropirimine, budotitane, amifostine, actinomycin, calcipotriol, calphostin C, calusterone, caracemide, carbetimer, floxuridine, idarubicin, ifosfamide, lomustine, mechlorethamine, melphalan, methotrexate, mitoxantrone, pliamycin, procarbazine, streptozocin and vinblastine.

In one embodiment, vaccine antigens can be, for example, tumor antigens or antigens from pathogenic organisms, such as viruses, bacteria, fungi and parasites. Thus, in some embodiments, the antigen is derived from a virus such as such but limited to, for example, hepatitis A virus (HAV), hepatitis B virus (HBV), hepatitis C virus (HCV), herpes simplex virus (HSV), human immunodeficiency virus (HIV), human papillomavirus (HPV), cytomegalovirus (CMV), influenza virus (e.g., influenza A virus), and rabies virus. In other embodiments, the antigen is derived from a bacterium such as, for example, cholera, diphtheria, tetanus, *streptococcus* (e.g., *streptococcus* A and B), *Streptococcus pneumonia* (e.g. over 90 serotypes, of which 88% that cause invasive disease are included in the 23-valent polysaccharide vaccine), pertussis, *Neisseria meningitidis* (e.g., meningitis A, B, C, W, Y), *Neisseria gonorrhoeae, Helicobacter pylori*, and *Haemophilus* influenza (e.g., *Haemophilus* influenza type B). In still other embodiments, the polypeptide-containing antigen is derived from a parasite such as, for example, a malaria parasite. Other antigens include those used to immunize against childhood diseases, such as polio, measles, mumps and rubella.

Yet other embodiments provide for the inclusion of agents suitable for the treatment of diabetes mellitus (types 1 and 2) and those suitable for the prevention and treatment of thrombotic and pro-thrombotic conditions (e.g. deep-vein thrombosis, pulmonary embolism, chronic atrial fibrillation, prosthetic heart valves, sickle cell). Non-limiting examples of such agents for diabetes include insulin and insulin analogs, (e.g., lispro (Humalog), Humulin (Isophane and Regular), Novolog (Aspart), Levemir (Detemir), Lantus (glargine) as well as other small molecules, such as metformin, rosiglitazone, pioglitazone and combinations containing such molecules (e.g., metformin and rosiglitazone, rosiglitazone and glimepiride). Other compounds that can be incorporated into the disclosed composition include: biguanides, such as metformin (Glucophage); thiazolidinediones (TZDs), such as rosiglitazone and pioglitazone; sulfonylureas, such as tolbutamide, (Orinase), acetohexamide (Dymelor), tolazamide (Tolinase), chlorpropamide (Diabinese), glipizide (Glucotrol), glyburide (Diabeta, Micronase, Glynase), glimepiride (Amaryl) or gliclazide (Diamicron); Nonsulfonylurea secretagogues, such as meglitinides (e.g., repaglinide (Prandin) and nateglinide (Starlix); and alpha-glucosidase inhibitors, such as miglitol (Glyset) or acarabose (Precose, Glucobay). Non-limiting examples of such agents for prevention or treatment of acute and/or chronic pre-thrombotic or thrombotic conditions include unfractionated and low molecular weight heparins such as ardeparin (Normiflo), bemiparin (Hibor, Ivor, Zibor, Badyket), certoparin (Sandoparin), dalteparin (Fragmin), enoxaparin (Lovenox, Clexane), nadroparin (Fraxiparin), parnaparin (Fluxum), reviparin (Clivarin) and tinzaparin (Innohep, Logiparin); Factor Xa inhibitors such as fondaparinux (Arixtra) and idraparinux sodium (SANORG 34006, SR 34006), rivaroxaban (BAY 59-7939, Xarelto), and apixaban (Eliquis); direct thrombin inhibitors such as lepirudin (Refludan), bivalirudin (Angiomax or Angiox), argatroban (Acova, Arganova, Argatra, Novastan) and dabigatran (Pradaxa, Pradax, Prazaxa); and vitamin K antagonists such as warfarin (Coumadin), Acenocoumarol (Sintrom, Sinthrome) and Phenprocoumon (Marcoumar, Marcumar, Falithrom). In certain embodiments, the co-polymer/enhancer formulation comprises a therapeutic agent at a concentration ranging from about 0.1 mM to about 3 mM, about 0.1 mM to about 2 mM, about 1 mM to about 1.5 mM, about 0.5 mM to about 2 mM, or about 0.5 mM to about 1.5 mM. Amounts of therapeutic agents incorporated into co-polymer/enhancer formulations disclosed herein can also be determined by those skilled in the art (e.g., based upon age, bioavailability of a therapeutic agent, etc.) such that the therapeutic agent is delivered to a subject in amounts that effect a therapeutic benefit to the subject.

Treatment of Cancer Via Topical Delivery of Therapeutics

Another aspect of the invention provides methods for enhanced delivery of therapeutic agents across the skin and/or mucosal surface. Preferably, the present invention enhances topical, non-invasive delivery of a broad range of small and large therapeutic agents of various classes and compositions as well as physicochemical properties (e.g. peptides, proteins, chemicals, nucleic acids), such as but not limited to cytotoxic decoy peptides, other chemotherapeutics and anti-tumor/anti-cancer agents, drugs for the treatment of diabetes mellitus, prevention and treatment of thrombotic and pro-thrombotic conditions, and antigens for the induction of a protective immune response to various vaccine antigens, as disclosed above.

In one embodiment the method comprises administering, to skin or mucosal surface of a subject, a co-polymer/enhancer formulation of the present invention. In a specific embodiment the method comprises administering, to skin or mucosal surface of a subject, a co-polymer/enhancer formulation comprising poloxamer 188 and propylene glycol, laurocapram and, optionally, one or more therapeutic agents.

The term "subject," as used herein, describes an organism, including mammals such as primates, to which treatment with the formulations according to the subject invention can be provided. Mammalian species that can benefit from the disclosed methods of treatment include, but are not limited to, apes, chimpanzees, orangutans, humans, monkeys; and domesticated animals such as dogs, cats, horses, cattle, pigs, sheep, goats, chickens, mice, rats, guinea pigs, and hamsters.

In certain embodiments the co-polymer/enhancer formulation of the present invention is administered to skin or mucosal surfaces including, but not limited to, cervix, vagina, anus, rectum, eye, ear, nose, thorax, vulva, larynx, and head and neck. In one embodiment the co-polymer/enhancer formulation of the present invention is topically administered to cervical dysplastic lesions of the ectocervix and proximal endocervical canal of women via an intravaginal route of mucosal delivery.

In one embodiment the present invention allows for topical delivery of therapeutics across keratinized apical layer of skin (stratum corneum) and/or mucosa. In another embodiment the present invention allows for topical delivery of therapeutics across non-keratinized surface of skin and/or mucosa. In one embodiment the present invention allows for topical delivery of therapeutics into, or across, multiple layers of cervical squamous epithelial cells. In one embodiment the present invention allows for topical delivery of therapeutics to the basal keratinocytes of skin and/or mucosa.

In a specific embodiment the present invention can be used to deliver therapeutics to penetrate the keratinized surface of the mouse cervical transformation zone. In a specific embodiment the present invention can be used to deliver therapeutics to penetrate non-keratinized human cervical transformation zone (T-zone) across multiple layers of squamous epithelial cells to reach the basal keratinocytes where HPV viral integration occurs.

As exemplified in the Example, the co-polymer/enhancer formulations of the present invention can deliver moderate sized peptides across the keratinized apical layer of mouse cervical T-zone. Mouse cervical transformation zone differs from that of human. Mouse cervix is completely internalized, whereas human has an ectocervix located on the vaginal surface. In addition, mouse cervix has a keratizined apical layer in the cervical T-zone, which begins from the vagino-cervical junction and ends at the squamo-columnar junction. Cervical T-zone is where most cervical cancers arise. The mouse keratinized cervical epithelium is comparable to keratinized skin. As exemplified in the Example, the co-polymer/enhancer formulation is capable of topical delivery and penetration of a 38 amino acid cytotoxic peptide across the mouse keratinized cervical squamous epithelium.

In certain embodiments, the present invention can be used for topical delivery of therapeutics across the keratin-rich, stratum corneum of skin to treat cutaneous neoplastic and non-neoplastic proliferative diseases including, but not limited to, HPV-associated pre-cancerous and cancerous conditions affecting vulva, vagina, anus, larynx, and head and neck, and melanoma, basal cell carcinoma, nasopharyngeal carcinoma associated with Epstein-Barr Virus infection and psoriasis.

In one embodiment the present invention can be used for topical delivery of chemotherapeutic and anti-cancer/anti-tumor agents for treatment of tumor or cancer including, but not limited to, human HPV-associated cervical cancer and its precursor lesions, such as pre-cancerous low-grade cervical dysplasia classified as cervical intraepithelial neoplasia stage I or II (CIN I, CIN II), high-grade dysplasia (CIN III), carcinoma in situ (CIS) and locally invasive or metastatic cervical cancer (11); prostate cancer; ovarian cancer; vulvar cancer; vaginal cancer or tumor; endometrial cancer; laryngeal carcinoma; nasal pharyngeal carcinoma; bladder cancer; nasopharyngeal carcinoma, skin cancer; and head and neck cancer.

In certain embodiments the present invention can be used for topical, non-invasive delivery of therapeutics for treatment of diseases or conditions, including hyperplastic skin lesions, such as, genital warts, psoriasis and keloids.

In certain embodiments the present invention can be used as a non-invasive topical transdermal or transmucosal delivery system (or device) applied to normal skin or mucosal surfaces to obviate the need for subcutaneous injection of therapeutic compounds.

Formulations and Formulations for Topical Administration

The subject invention also provides for therapeutic or pharmaceutical formulations comprising the co-polymer/enhancer formulation in a form that can be combined with a pharmaceutically acceptable carrier. In a preferred embodiment the therapeutic or pharmaceutical formulation is solid or semi-solid at room temperature and melts at a temperature slightly below desired physiological temperatures.

The term "carrier" refers to a diluent, adjuvant, excipient or vehicle with which the compound is administered. Such pharmaceutical carriers can be sterile liquids, such as water and oils, including those of petroleum oil such as mineral oil, vegetable oil such as peanut oil, soybean oil and sesame oil, animal oil or oil of synthetic origin.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The therapeutic formulation, if desired, can also contain minor amounts of wetting, emulsifying or pH buffering agents. These formulations can take the form of creams, foam, patches, lotions, drops, sprays, gel, oils, aerosol, powders, ointment, solutions, suspensions, emulsion and the like. The formulation can be formulated with traditional binders and carriers such as triglycerides. Examples of suitable pharmaceutical carriers are described in "Remington's Pharmaceutical Sciences" by E. W. Martin. Such formulations contain a therapeutically effective amount of the therapeutic formulation, together with a suitable amount of carrier so as to provide the form for proper administration to the patient. The formulation should suit the mode of administration.

The subject invention also provides for the modification of the ingredient such that it is more stable once administered to a subject, i.e., once administered it has a longer time period of effectiveness as compared to the unmodified form. Such modifications are well known to those of skill in the art, e.g., microencapsulation, etc.

The amount of the therapeutic or pharmaceutical formulation of the invention which is effective in the treatment of a particular disease, condition or disorder will depend on the route of administration and the seriousness of the disease, condition or disorder and should be decided according to the judgment of the practitioner and each patient's circumstances.

Further, the present invention provides kits containing therapeutic agents such as, lyophilized cytotoxic decoy peptides, vehicle and/or co-polymer/enhancer formulations. Preferably, the formulations of the present invention are stable in a wide range of temperatures below the desired melting temperature. In one embodiment the active therapeutic agents can be reconstituted by mixing pre-measured quantities of each component immediately prior to use.

EXAMPLES

Following are examples that illustrate procedures for practicing the invention. These examples should not be construed as limiting. All percentages are by weight and all solvent mixture proportions are by volume unless otherwise noted.

Example 1

Thermo-Sensitive, Mucoadhesive, and Penetration-Enhancing Formulations

To create co-polymer/enhancer formulations with desired thermo-sensitive properties, USP grade poloxamer 188 (P188) and propylene glycol (PG) were mixed at various ratios (100/0, 80/20, 70/30, 50/50 and 0/100) and heated to 60° C. The co-polymer/enhancer preparations were suctioned into pre-warmed (60° C.) Silastic tubing (1/8$^{th}$-inch inner diameter; Fisher, Pittsburgh, Pa.), solidified at room temperature and extruded from the tube with compressed air (12). 3 mm samples were cut from the solid "rope" with a scalpel.

The thermal profile of the P188/PG co-polymer preparations was determined using a DSC 6200/Exstar 6000 (Seiko Instruments) Differential Scanning calorimeter. To obtain co-polymer preparations that have the desired melting point (30-37° C.) in the presence of 1 mM of various decoy peptides, DSC 6200 was programmed with 3 cycles of heating at 10° C./min and cooling at 50° C./min, with 2 min equilibration times between heating/cooling cycles. Measurements were taken at a temperature range of −25-65° C.

The DSC curves did not exhibit dual peaks, indicating that the P188/PG co-polymer preparations were in a homogeneous phase. The co-polymer with an 80/20 ratio of P188/PG exhibited the desired thermal property, that is, solid at room temperature and instantly melted at a temperature slightly below the physiological temperature of 37° C.

The P188/PG (80/20 ratio) co-polymer was then used to deliver FITC-tagged 38 amino acid cytotoxic decoy peptides. The P188/PG co-polymer (80/20 ratio) alone was unable to penetrate the keratinized apical layer of the mouse cervix, as determined by direct visualization using fluorescence microscopy (data not shown).

Laurocapram is a non-toxic enhancer of cutaneous penetration (13, 14). It is among a class of "penetration modifiers" (15, 16) that, depending on the vehicle formulation, can enhance or retard the penetration of human stratum corneum. DSC and spectral analysis revealed that penetration modifier formulations (e.g., laurocapram) disrupt and fluidize the stratum corneum lipid bilayers (17). Since 1984, laurocapram has been widely used as a safe penetration enhancer and has been formulated with propylene glycol—a mucoadhesive and dermoadhesive agent (17, 18).

0.4 M laurocapram (17) was added to the P188/PG preparations. The DSC curves (FIG. 1) show that the formulation composed of 1 mM of the cytotoxic decoy peptide *Br1, a 70/30 ratio of P188/PG co-polymer and 0.4 M laurocapram has the desired thermo-sensitive properties for delivery of cytotoxic decoy peptides (delivery of *Br2 is not shown). As shown below, this new formulation can enhance penetration of cytotoxic decoy peptides across the keratinized surface of mouse cervical mucosa, which resembles the stratum corneum of skin.

The entire mouse cervical T-zone begins from the cervicovaginal junction to the termination of the cervical T-zone, which is approximately one-third of the distance into one of the 2 cervical/uterine horns. To achieve topical delivery of decoy peptides into the entire mouse cervical T-zone, a solid FITC-tagged decoy peptide-containing co-polymer/enhancer rod was manually delivered into the endocervical canal and into one of the 2 cervical/uterine horns of a 7 month old K14E6 homozygous female transgenic mouse expressing the HPV type 16 E6 oncoprotein that synergizes with 17β-estradiol to induce low-grade dysplasia (CIN I, II) in situ that closely mimics the step-wise development of human cervical cancer; the "untreated" cervical served as an internal control.

After animals were anesthetized, a "speculum" comprised of a standard P-100 pipette tip with the tip cut off at the midpoint along its length was inserted into the vagina to expose the opening of the cervical canal. A three-fourth inch long, 24-gauge catheter (Teruma Surflush; inner diameter 0.47 mm) with the trocar removed was fit onto a compatible P-10 micropipette. The catheter was loaded with the peptide-containing, liquid co-polymer/enhancer formulation to a length that approximates the entire cervical T-zone and extends across the squamo-columnar junction into the uterine horn.

After the co-polymer/enhancer formulation solidified into rod shape at room temperature, the tip of the catheter was inserted into the entrance of the cervix, and the solid rod was pushed into the cervical canal by the trocar; meanwhile, the catheter tip was withdrawn so that, at the end of the procedure, the rod protruded ~2 mm outside of the cervical canal. It is observed that the co-polymer/enhancer formulation underwent phase transition from a solid rod into a consistent gel-like formulation, without leakage from the cervical opening.

Six hours after peptide delivery the animals were euthanized. The entire reproductive tract was surgically removed, fixed with formalin and embedded for histological sectioning as described (19).

1 mM FITC-conjugated *Br1 was used for direct visualization of peptide delivery by fluorescence microscopy. Fluorescence microscopy showed that both formulations, which contain P188 and PG, are mucoadhesive to the keratinized apical surface.

FIG. 2 shows a direct comparison between the penetration property of the lauracopram-containing and the non-lauracopram-containing formulation in a single mouse reproductive tract. A rod consisting of the 80/20 P188/PG formulation (without lauracopram) was introduced high up into the right cervical/uterine horn under ultrasound guidance, while a rod consisting of the 70/30 formulation and 0.4M lauracopram was introduced into the left cervical/uterine horn.

Figures 2A, 2B:
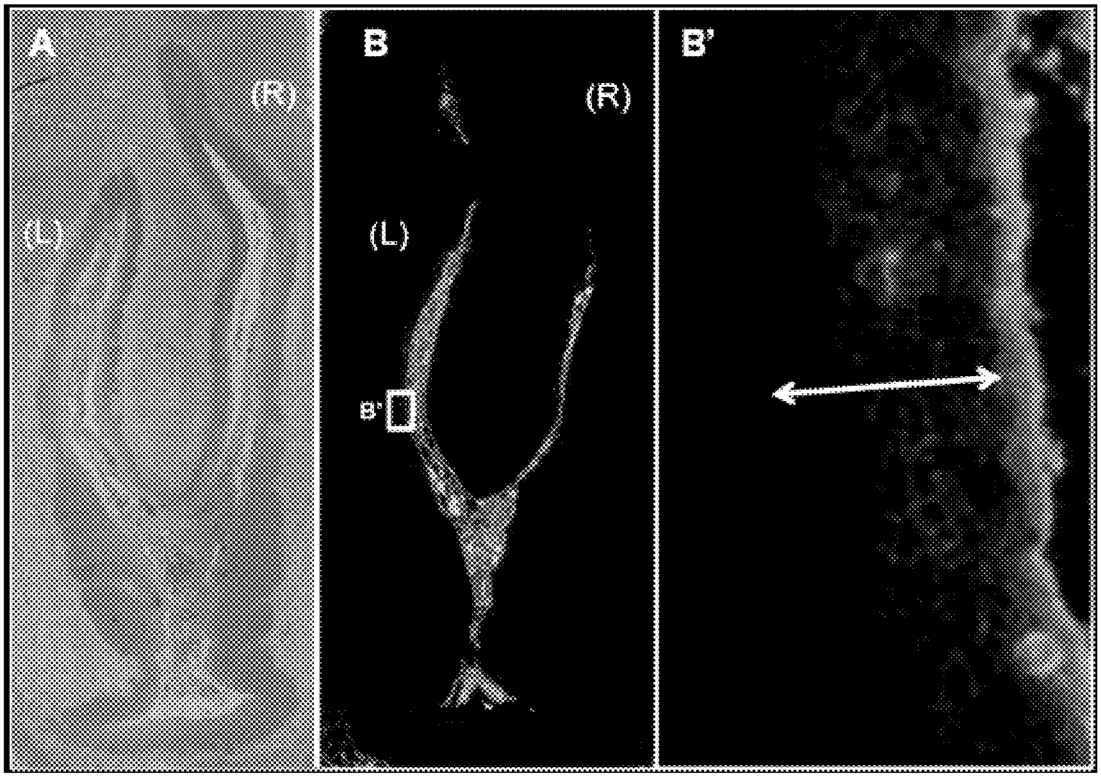
FIGS. 2A, 2B and 2B' show micrographs of mouse cervical squamous epithelium (original magnification 10×). (A) H&E stain of squamous epithelium lining the cervical canal and its left and right branches. The squamo-columnar junction is not shown in this section. (B) Fluorescence micrograph of a consecutive section, showing that the P188/PG-containing drug delivery formulation melts and adheres to the cervical mucosal surface in both cervical/uterine horns. (B') Enlargement of detail of box in panel B, showing a gradient of laurocapram-enhanced penetration 6 hours after insertion of the peptide-containing drug delivery formulation across the thickness delineated by the arrow in the drug delivery formulation containing P188, PG and LP (left cervical canal), but not in the absence of LP (right cervical canal). Intense staining of mucoadherent FITC-conjugated *Br1 is observed on the mucosal surface of both cervical canals and uterine horns. Intense staining shows that FITC-conjugated *Br1 melts and adheres to the mucosal surface of the cervical transformation zone spanning the endocervical canal and endocervix leading to both uterine horns.

Specifically, penetration across the apical keratin layer of cervical squamous epithelium was only observed in the left cervical/uterine horn, where the rod contained 0.4 M lauracopram (FIG. 2B, 2B'). It is evident that the lauracopram-containing rod penetrated through multiple layers of cervical squamous epithelial cells, when comparing fluorescence microscopic imaging of an unstained section (FIG. 2B) with light microscopic examination of a consecutive H&E stained section (FIG. 2A).

All patents, patent applications, provisional applications and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

1. Garcia M, Jemal, A., Ward, E. M., Center, M. M., Hao, Y., Siegel, R. L., and Thun, M. J. 2008. Global Cancer Facts & Figures 2007. *Atlanta, Ga.: American Cancer Society*

4. de Sanjose S et al., Human papillomavirus genotype attribution in invasive cervical cancer: a retrospective cross-sectional worldwide study. *Lancet Oncol* 11: 1048-56
5. Munoz N, Bosch F X, de Sanjose S, Herrero R, Castellsague X, Shah K V, Snijders P J, Meijer C J. 2003. Epidemiologic classification of human papillomavirus types associated with cervical cancer. *N Engl J Med* 348: 518-27
6. Walboomers J M, Jacobs M V, Manos M M, Bosch F X, Kummer J A, Shah K V, Snijders P J, Peto J, Meijer C J, Munoz N. 1999. Human papillomavirus is a necessary cause of invasive cervical cancer worldwide. *J Pathol* 189: 12-9
8. Hsu S I, Yang C M, Sim K G, Hentschel D M, O'Leary E, Bonventre J V. 2001. TRIP-Br: a novel family of PHD zinc finger- and bromodomain-interacting proteins that regulate the transcriptional activity of E2F-1/DP-1. *EMBO J* 20: 2273-85
9. Sim K G, Zang Z, Yang C M, Bonventre J V, Hsu S I. 2004. TRIP-Br links E2F to novel functions in the regulation of cyclin E expression during cell cycle progression and in the maintenance of genomic stability. *Cell Cycle* 3: 1296-304
10. Zang Z J, Sim K G, Cheong J K, Yang C M, Yap C S, Hsu S I. 2007. Exploiting the TRIP-Br Family of Cell Cycle Regulatory Proteins as Chemotherapeutic Drug Targets in Human Cancer. *Cancer Biol Ther* 6
11. DeMay M. 2007. *Practical principles of cytopathology (Revised edition)*. Chicago: American Society for Clinical Pathology Press
13. Stoughton R B. 1982. Enhanced percutaneous penetration with 1-dodecylazacycloheptan-2-one. *Arch Dermatol* 118: 474-7
14. Stoughton R B, and McClure, W. O. 1983. Azone; a new non-toxic enhancer of cutaneous penetration. *Drug Development and Industrial Pharmacy* 9: 725-44
15. Kaushik D, Batheja P, Kilfoyle B, Rai V, Michniak-Kohn B. 2008. Percutaneous permeation modifiers: enhancement versus retardation. *Expert Opin Drug Deliv* 5: 517-29
16. Kaushik D, Costache A, Michniak-Kohn B. 2010. Percutaneous penetration modifiers and formulation effects. *Int J Pharm* 386: 42-51
17. Kaushik D, Michniak-Kohn B. 2010. Percutaneous penetration modifiers and formulation effects: thermal and spectral analyses. *AAPS Pharm Sci Tech* 11: 1068-83
18. Spruance S L, McKeough M, Sugibayashi K, Robertson F, Gaede P, Clark D S. 1984. Effect of azone and propylene glycol on penetration of trifluorothymidine through skin and efficacy of different topical formulations against cutaneous herpes simplex virus infections in guinea pigs. *Antimicrob Agents Chemother* 26: 819-23
19. Riley R R, Duensing S, Brake T, Munger K, Lambert P F, Arbeit J M. 2003. Dissection of human papillomavirus E6 and E7 function in transgenic mouse models of cervical carcinogenesis. *Cancer Res* 63: 4862-71

What is claimed is:

1. A composition for topical delivery of therapeutics across the skin or mucosal surfaces comprising poloxamer 188, propylene glycol, laurocapram and a vaccine antigen selected from the group consisting of: tumor antigens, viral antigens, bacterial antigens, fungal antigens, parasite antigens and allergens.

2. A composition for topical delivery of therapeutics across the skin or mucosal surfaces comprising poloxamer 188, propylene glycol, laurocapram and a therapeutic agent, wherein the therapeutic agent is insulin, an insulin analog, a biguanide, a thiazolidinedione, a sulfonylurea, a nonsulfonylurea secretagogue, an alpha-glucosidase inhibitor or a combination thereof.

3. The composition for topical delivery of therapeutics across the skin or mucosal surfaces according to claim 2, wherein said insulin analog is Lispro (Humalog), Humulin (Isophane and Regular), Novolog (Aspart), Levemir (Detemir), or Lantus (glargine).

4. A composition for topical delivery of therapeutics across the skin or mucosal surfaces comprising poloxamer 188, propylene glycol, laurocapram and a therapeutic agent, wherein the therapeutic agent is metformin, rosiglitazone, pioglitazone, troglitazone, tolbutamide, acetohexamide, tolazamide, chlorpropamide, glipizide, glyburide, glimepiride, gliclazide, repaglinide, nateglinide miglitol, acarabose or a combination thereof.

5. A method of treating diabetes comprising the topical or mucosal administration of the composition according to claim 2 to a subject having diabetes in an amount effective to treat diabetes.

6. A method of inducing an immune response in a subject comprising the topical or mucosal administration of the composition according to claim 1 to a subject in an amount effective to induce an immune response to an vaccine antigen contained within said formulation, wherein said vaccine antigen is selected from the group consisting of: tumor antigens, viral antigens, bacterial antigens, fungal antigens, parasite antigens and allergens.

7. A method of treating diabetes comprising the topical or mucosal administration of the composition according to claim 4 to a subject having diabetes in an amount effective to treat diabetes.

* * * * *